United States Patent
Rynerson

(10) Patent No.: US 10,821,022 B2
(45) Date of Patent: Nov. 3, 2020

(54) INSTRUMENT FOR TREATING AN OCULAR DISORDER

(71) Applicant: BlephEx, LLC, Franklin, TN (US)

(72) Inventor: James M. Rynerson, Alvaton, KY (US)

(73) Assignee: BlephEx, LLC, Franklin, TN (US)

(*) Notice: Subject to any disclaimer, the term of this patent is extended or adjusted under 35 U.S.C. 154(b) by 0 days.

(21) Appl. No.: 13/949,365

(22) Filed: Jul. 24, 2013

(65) Prior Publication Data

US 2014/0052164 A1    Feb. 20, 2014

Related U.S. Application Data

(63) Continuation-in-part of application No. 13/556,729, filed on Jul. 24, 2012, now Pat. No. 9,039,718.

(51) Int. Cl.
*A61F 9/007* (2006.01)
*A61F 13/38* (2006.01)

(52) U.S. Cl.
CPC .......... *A61F 9/00709* (2013.01); *A61F 13/38* (2013.01)

(58) Field of Classification Search
CPC .... A61F 13/38; A61F 9/00709; A61F 11/006; A61M 35/006; A61B 17/225–2258; A61B 17/320068–2017; A61B 17/22004–2017; Y10T 279/17863; Y10T 279/17888; Y10T 403/7035; Y10T 403/7098;
(Continued)

(56) References Cited

U.S. PATENT DOCUMENTS

| | | | | |
|---|---|---|---|---|
| 111,265 A | * | 1/1871 | Shoemaker | E21B 10/633 175/413 |
| 1,100,504 A | * | 6/1914 | Taft | B65H 75/14 242/118.6 |

(Continued)

FOREIGN PATENT DOCUMENTS

| | | |
|---|---|---|
| CA | 2257040 A1 | 6/2000 |
| CN | 8620449 | 4/1987 |

(Continued)

OTHER PUBLICATIONS

Algerbrush II Quick Reference Catalog, dated Oct. 2012, available at www.rheinmedical.com/wp-content/uploads/2012/10/AlgerbrushCatalog1333AHBC.pdf.*

(Continued)

*Primary Examiner* — Tan-Uyen T Ho
*Assistant Examiner* — Charles M Wei
(74) *Attorney, Agent, or Firm* — Wilson Sonsini Goodrich & Rosati

(57) ABSTRACT

An instrument for removing debris from an eye during the treatment of an ocular disorder has a swab and a rigid member. The swab includes a tip portion sized to provide access to the debris on an eyelid of the eye. The rigid member has a distal end portion affixed to the swab and a proximal end portion with a cross-sectional member profile. The cross-sectional member profile is non-circular and has a first groove. The first groove extends longitudinally along the proximal end portion for cooperating with a chuck such that rotation of the proximal end portion within the chuck is inhibited.

6 Claims, 5 Drawing Sheets

(58) Field of Classification Search
CPC ......... Y10T 403/7016; Y10T 403/7039; Y10T 403/7026
USPC .................... 606/162, 107; 128/898; 15/97.1
See application file for complete search history.

(56) References Cited

U.S. PATENT DOCUMENTS

| | | | | |
|---|---|---|---|---|
| 1,554,317 | A * | 9/1925 | Worthing | B25G 3/02 403/277 |
| 1,707,353 | A * | 4/1929 | Fraser | F16K 31/60 251/292 |
| 1,832,554 | A * | 11/1931 | Holstein | G05G 1/12 403/354 |
| 2,006,539 | A | 7/1935 | Deford | |
| 2,546,061 | A * | 3/1951 | De Beauvais | H01R 13/187 403/326 |
| 2,766,471 | A * | 10/1956 | McKenzie | B26B 5/00 15/105 |
| 2,766,650 | A * | 10/1956 | Capra | B25B 7/02 279/93 |
| 3,029,672 | A * | 4/1962 | Lowenborg | E21B 6/06 173/111 |
| 3,507,508 | A * | 4/1970 | Andrews | B23B 31/1075 279/83 |
| 3,517,754 | A * | 6/1970 | Hughes | E21B 17/073 173/104 |
| D262,739 | S | 1/1982 | Nitshke | |
| D286,438 | S | 10/1986 | Lichtman | |
| 4,778,457 | A | 10/1988 | York | |
| 4,838,851 | A | 6/1989 | Shabo | |
| 4,883,454 | A | 11/1989 | Hamburg | |
| D306,347 | S | 2/1990 | Gyurik | |
| 4,913,682 | A | 4/1990 | Shabo | |
| 4,955,896 | A | 9/1990 | Freeman | |
| 5,176,694 | A * | 1/1993 | Price | A61F 9/00709 606/162 |
| 5,456,265 | A | 10/1995 | Yim | |
| 5,458,427 | A * | 10/1995 | Simond | A63C 11/221 280/820 |
| 5,498,077 | A * | 3/1996 | Krzywdzjak | B01F 7/1695 366/247 |
| 5,588,497 | A * | 12/1996 | Thorburn | E21B 10/56 175/413 |
| 5,632,756 | A | 5/1997 | Kruglick | |
| 5,690,618 | A | 11/1997 | Smith et al. | |
| D401,332 | S | 11/1998 | Picha | |
| 5,904,390 | A | 5/1999 | Emery et al. | |
| 5,974,615 | A | 11/1999 | Schwarz-Hartmann et al. | |
| 6,036,198 | A * | 3/2000 | Kramer | B23H 7/26 219/69.15 |
| 6,116,900 | A | 9/2000 | Ostler | |
| 6,536,066 | B2 | 3/2003 | Dickie | |
| 7,384,405 | B2 | 6/2008 | Rhoades | |
| D588,697 | S | 3/2009 | Hickok | |
| D589,620 | S | 3/2009 | Hickok | |
| D645,140 | S | 9/2011 | Peuker et al. | |
| D701,304 | S | 3/2014 | Lair et al. | |
| D701,308 | S | 3/2014 | Brannon | |
| D705,426 | S | 5/2014 | Fiorina et al. | |
| 9,039,718 | B2 | 5/2015 | Rynerson | |
| 9,675,516 | B2 | 6/2017 | Parsloe | |
| 2004/0067098 | A1* | 4/2004 | Sun | A47B 13/021 403/315 |
| 2004/0172035 | A1* | 9/2004 | Parmigiani | A61C 8/0089 606/80 |
| 2005/0132513 | A1 | 6/2005 | Eliav et al. | |
| 2006/0116355 | A1 | 6/2006 | Van Breen | |
| 2007/0016255 | A1* | 1/2007 | Korb | A61F 9/00772 607/1 |
| 2007/0049860 | A1* | 3/2007 | Seminara | A61B 17/00234 604/1 |
| 2007/0060988 | A1* | 3/2007 | Grenon | A61F 9/00 607/96 |
| 2007/0231353 | A1 | 10/2007 | Gilbard et al. | |
| 2008/0188877 | A1 | 8/2008 | Hickingbotham | |
| 2008/0221533 | A1* | 9/2008 | Matityahu | A44C 15/0095 604/290 |
| 2008/0260563 | A1* | 10/2008 | Refenius | F04C 15/0076 418/259 |
| 2009/0112242 | A1 | 4/2009 | Kao | |
| 2010/0256552 | A1* | 10/2010 | Korb | A61F 9/00772 604/20 |
| 2011/0137214 | A1 | 6/2011 | Korb et al. | |
| 2011/0144562 | A1 | 6/2011 | Heeren et al. | |
| 2011/0160635 | A1* | 6/2011 | Baschnagel | A61F 13/38 604/2 |
| 2012/0065556 | A1 | 3/2012 | Smith et al. | |
| 2013/0058710 | A1* | 3/2013 | Fan | F16D 1/101 403/348 |
| 2013/0081518 | A1* | 4/2013 | Scheid | B23B 47/00 81/58.2 |
| 2013/0331768 | A1 | 12/2013 | Nichamin | |
| 2014/0031845 | A1 | 1/2014 | Rynerson | |
| 2014/0214062 | A1 | 7/2014 | Rynerson et al. | |
| 2014/0221908 | A1* | 8/2014 | Sonsino | A61F 9/00772 604/28 |
| 2019/0209373 | A1 | 7/2019 | Rynerson | |

FOREIGN PATENT DOCUMENTS

| | | |
|---|---|---|
| CN | 253831 | 3/2003 |
| CN | 201168118 Y | 12/2008 |
| CN | 20150521 | 6/2010 |
| CN | 201362154 U | 1/2011 |
| CN | 201692153 U | 1/2011 |
| JP | H06-261839 A | 9/1994 |
| JP | 10108801 A | 4/1998 |
| WO | 9633676 A1 | 10/1996 |
| WO | WO/2009/066077 † | 5/2009 |
| WO | WO-2009066077 A1 | 5/2009 |
| WO | WO-2010149959 A1 | 12/2010 |
| WO | 2012092320 A2 | 7/2012 |
| WO | 2012092320 A3 | 7/2012 |

OTHER PUBLICATIONS

"Connector standard sheets." Wikipedia. <http://en.wikipedia.org/wiki/IEC_60320>. Accessed Sep. 13, 2018.*
Chinese Intellectual Property Office, English Translation of First Office Action issued in related Chinese Application No. 201380049077.1, dated Dec. 28, 2015 (4 pages).
Sue Stevens (NIH), How to Clean Eyelids, Community Eye Health Journal, 24(75):20, Sep. 2011 (15 pages) <http://www.cehjournal.org/article/how-to-clean-eyelids/> and <http://www.ncbi.nlm.nih.gov/pmc/articles/PMC3218399/>.
The Alger Company, AlgerBrush II Operating Instructions. Apr. 2012 (2 pages).
The Alger Company, AlgerBrush Product Spec Sheet, Jun. 24, 2012 (1 page).
Alger Equipment Company, Algerbrush II, Introduction, Product Info, About Us, FAQ's, <https://web.archive,org/web/20101121065649/http://www.algercompany.co> (2009); <https://web.archive/org/web/20100103204839/http://www.algercompany.co> (2009); <https://web.archive.org/web/20100817072535/http://www/algercompany.co> (2009); <https://web.archive.org/web/20101030135414/http://www.algercompany.co> (2009); <https://web.archive.org/web/20101029151415/http://www.algercompany.co> (2009);and <https://web/archive.org/web/20101030135409/http://www.algercompany.co/brush/Bnews.htm>.
James E. Key, MD, A Comparative Study of Eyelid Cleaning Regimens in Chronic Blepharitis, Contact Lens Association of Opthalmologists Journal, Jul. 1996, vol. 22 No. 3, (pp. 209-212).
Gerd Geerling et al., the International Workshop on Meibomian Gland Dysfunction: Report of the Subcommittee on Management and Treatment of Meibomian Gland Dysfunction, The Association for Research in Vision and Ophthalmology, Inc., IOVS Special Issue 2011, vol. 52, No. 4 (pp. 2050-2064).

(56) References Cited

OTHER PUBLICATIONS

Eric Knop et al., The International Workshop on Meibomian Gland Dysfunction: Report of the Subcommittee on Anatomy, Physiology, and Pathophysiology of the Meibomian Gland, The Association for Research in Vision and Dphthalmology, Inc., IOVS Special Issue 2011, vol. 52, No. 4 (pp. 1938-1978).
*Blephex LLC v. Pain Point Medical Systems, Inc., d/b/a MiBo Medical Group Inc.*, Case No. 3:16-cv-00410N, USDC, Northern District of Texas, Dallas Division, Defendant's Invalidity Contentions, filed Jun. 24, 2016 (15 pages).
Eurasian Patent Office, Official Action issued in corresponding Eurasian Application No. 201590259 dated Oct. 4, 2016, 10 pp., including English translation.
Japanese Patent Office, Office Action issued in corresponding Japanese Patent Application No. 2015-524423, dated May 15, 2017, English translation only (7 pages).
The Eurasian Patent Organization, Official Action issued in corresponding Eurasian Patent Application No. 201590259, dated Jul. 11, 2017, English Translation only (2 pages).
Australian Government, IP Australia, Notice of acceptance for patent application issued in corresponding Australian Application No. 2013295781, dated Sep. 20, 2017 (3 pages).
Algerbrush II Quick Reference Catalog, [cited Oct. 2012]. Available from [www.rheinmedical.com/wpcontent/uploads/2012/10/AlgerbrushCatalog1333AHBC.pdf].
OCuSOFT [cited Jan. 8, 2015]. Available from: [http://www.ocusoft.com/Foreign-body-Removai-AKGERBRUSH-II-CHUCK-P4666.aspx] Screen capture of page submitted herewith as Algerbrush II Chuck with bilobal fitting.
Rhein Medical, Inc., [cited Jan. 8, 2015]. Retrieved form the internet at [http://www.rheinmedical.com/products-page/algerbrushes/08-13154-algerbrush-ii-chuch-2-5mm-round-fine-gruit-diamond-ball//] Screen capture of page submitted herewith as Algerbrush II chuck and round burr.
The Alger Co., Inc., [cited Dec. 22, 2014]. Available from [http://www.algercompany.com/brush/pdf-file/], click on "Operating/Sterilization Procedures" then click on "Algerbrush II Operating Instruction Rev. 3 2012" to retrieve pdf submitted herewith as "Aigerbrush-11-Operating _instruct. 2012".
The Alger Co., Inc., [cited Dec. 22, 2014]. Available from [http://www.algrecompany.com/brush/2013/01/02/lhe-algerbrush-ii-2/] Screen capture of page submitted herewith as Algerbrush II Product Page.
U.S. Appl. No. 13/556,729 Notice of Allowance dated Apr. 6, 2015.
U.S. Appl. No. 13/556,729 Notice of Allowance dated Apr. 23, 2015.
U.S. Appl. No. 13/556,729 Notice of Allowance dated Mar. 11, 2015.
U.S. Appl. No. 13/556,729 Office Action dated Sep. 19, 2014.
U.S. Appl. No. 14/229,275 Office Action dated Jun. 5, 2015.
U.S. Appl. No. 14/229,275 Office Action dated May 15, 2017.
The Alger Company, Inc. "AlgerBrush II," available at http://www.algercompany.com/download/ab_web/Alberbrush3_8.pdf, accessed on Mar. 30, 2012, 1 page.
1FORTHEMONEY, et al. "Blepharitis," available at http://en.wikipedia.org/w/index.php?oldid=474399644, accessed on Mar. 12, 2012, 6 pp.
International Searching Authority, International Search Report and Written Opinion, International Application No. PCT/US2013/051850, dated Oct. 14, 2013, 11 pages.
Advertising material for the AlgerBrush II. Bates No. PPM000709-PPM000710. 2 pages.
AlgerBrush II device. Bates No. PPM000714-PPM000716. 3 pages.
AlgerBrush II device. Bates No. PPM002763. 1 page.
AlgerBrush II device. Bates No. PPM002764. 1 page.
Blephex Advertisement. Bates No. B000584. 1 page.
*Blephex LLC v. Pain Point Medical Systems, Inc., d/b/ MiBo Medical Group Inc.*, Case No. 3:16-cv-00410N, Usdc, Northern District of Texas, Dallas Division, Defendant's Amended Invalidity Contentions, filed Oct. 11, 2018. 59 pages.

*Blephex LLC v. Pain Point Medical Systems, Inc., d/b/a MiBo Medical Group Inc.*, Case No. 3:16-cv-00410N, USDC, Northern District of Texas, Dallas Division, Claim Construction Order, Issued Apr. 23, 2019. 12 pages.
Blephex Owner's Manual. Bates No. B000516-6000521. 6 pages.
Brown et al.: Corneal Rust Removal by Electric Drill. British J. Ophthal. 59: 586-589 (1975). Bates No. PPM002809-PPM002813. 5 pages.
Co-pending U.S. Appl. No. 16/590,228, filed Oct. 1, 2019.
Cotton swab. Bates No. PPM002765. 1 page.
Dremel brand rotary tool variable speed setting. Bates. No. PPM002770. 1 page.
Dremel brand rotary tool. Bates. No. PPM002766. 1 page.
Dremel brand rotary tool. Bates. No. PPM002767. 1 page.
Dremel brand rotary tool. Bates. No. PPM002768. 1 page.
Dremel brand rotary tool. Bates. No. PPM002769. 1 page.
Dremel Instructional Safety Manual. Bates No. PPM002771-PPM002793. 23 pages.
Dremel Quick Start Book. Bates No. PPM002794-PPM002804. 11 pages.
European search report with written opinion dated Mar. 26, 2019 for EP Application No. 18185867.
Greiner, et al. Effects of eyelid scrubbing on the lid margin. CLAO J. Apr. 1999;25(2):109-13.
*Myco Ind., Inc., v. Blephex, LLC*, Case No. 2:19-cv-10645, USDC, Eastern District of Michigan, Southern Division, Opinion and Order Granting Plaintiff's Amended Motion for Preliminary Injunction, issued Aug. 27, 2019. 24 pages.
Office action dated May 2, 2019 for U.S. Appl. No. 16/352,758.
The Alger Company. Algerbrush and Algerbrush II. Bates No. PPM00283-PPM00292. 10 pages.
Weck-Cel brand surgical sponge. Bates No. PPM002805-PPM002808. 4 pages.
*BlephEx, LLC.v. Myco Industries, Inc.*and John R. Choate. Civil Action No. 2:19-cv-13089.
*BlephEx, LLC.v. Myco Industries, Inc.*and John R. Choate. Civil Action No. 2:19-cv-13089. BlephEx, LLC's Reply in Further Support of Motion for a Preliminary Injunction. Dec. 11, 2019.
*BlephEx, LLC.v. Myco Industries, Inc.*and John R. Choate. Civil Action No. 2:19-cv-13089. Declaration of Dr. James M. Rynerson in Support of BlephEx, LLC's Motion for a Preliminary Injunction. Nov. 7, 2019.
*BlephEx, LLC.v. Myco Industries, Inc.*and John R. Choate. Civil Action No. 2:19-cv-13089. Declaration of Matthew D. Robson in Support of BlephEx, LLC's Motion for a Preliminary Injunction. (Including the following Exhibits 1-30, 32-62). Nov. 7, 2019.
Exhibit 1: A true and correct copy of U.S. Pat. No. 10,449,087. Nov. 7, 2019.
Exhibit 2: A true and correct excerpted copy of the prosecution history of U.S. Pat. No. 10,449,087. Nov. 7, 2019.
Exhibit 3: A true and correct excerpted copy of U.S. Appl. No. 13/556,729. dated Nov. 7, 2019.
Exhibit 4: A true and correct copy of U.S. Pat. No. 9,039,718. Nov. 7, 2019.
Exhibit 5: A true and correct copy of the Final Written Decision of the Patent Trial and Appeal Board of the United States Patent and Trademark Office regarding U.S. Pat. No. 9,039,718, dated Feb. 28, 2018. Nov. 7, 2019.
Exhibit 6: A true and correct excerpted copy of Myco Industries, Inc.'s ("Myco") Mar. 15, 2019 Motion for Preliminary Injunction from *Myco Industries, Inc. v. BlephEx, LLC*, 2:19-cv-10645-GAD-EAS, Dkt. 10 (E.D. Mich.). Nov. 7, 2019.
Exhibit 7: A true and correct copy of the Court's Aug. 27, 2019 Order regarding Myco's Motion for Preliminary Injunction from *Myco Industries, Inc. v. BlephEx, LLC*, 2:19-cv-10645- GAD-EAS, Dkt. 56 (E.D. Mich.). Nov. 7, 2019.
Exhibit 8: A true and correct copy of Myco's Oct. 3, 2019 Opening Claim Construction Brief from *Myco Industries, Inc. v. BlephEx, LLC*, 2:19-cv-10645-GAD-EAS, Dkt. 67 (E.D. Mich.). Nov. 7, 2019.

(56) References Cited

OTHER PUBLICATIONS

Exhibit 9: A true and correct copy of BlephEx's Oct. 3, 2019 Opening Claim Construction Brief from *Myco Industries, Inc.* v. *BlephEx, LLC*, 2:19-cv-10645-GAD-EAS, Dkt. 68 (E.D. Mich.). Nov. 7, 2019.
Exhibit 10: A true and correct excerpted copy of the Declaration of Dr. Penny Asbell submitted in support of BlephEx's proposed claim constructions, dated Aug. 29, 2019, from *Myco Industries, Inc.* v. *BlephEx, LLC*, 2:19-cv-10645-GAD-EAS (E.D. Mich.). Nov. 7, 2019.
Exhibit 11: A true and correct excerpted copy of the transcript of the Sep. 11, 2019 deposition of Dr. Steve Silberberg from *Myco Industries, Inc.* v. *BlephEx, LLC*, 2:19-cv-10645- GAD-EAS (E.D. Mich.). Nov. 7, 2019.
Exhibit 12: A true and correct copy of Exhibit 14 to the Sep. 11, 2019 deposition of Dr. Steve Silberberg from *Myco Industries, Inc.* v. *BlephEx, LLC*, 2:19-cv-10645-GAD-EAS (E.D. Mich.). Nov. 7, 2019.
Exhibit 13: A true and correct excerpted copy of Dorland's Illustrated Medical Dictionary, 30$^{th}$Ed. (2003). Nov. 7, 2019.
Exhibit 14: A true and correct copy of a web page titled "What Makes up the Eyelid Margin?" dated Jan. 29, 2014 from the website of the American Academy of Ophthalmology. Nov. 7, 2019.
Exhibit 15: A true and correct copy of a web page titled "Eyelid margin" from the website of the American Academy of Ophthalmology. Nov. 7, 2019.
Exhibit 16: A true and correct copy of an article by Nelson et al. titled "The International Workshop on Meibomian Gland Dysfunction: Report of the Definition and Classification Subcommittee" by (2011) downloaded from iovs.arvojournals.org. Nov. 7, 2019.
Exhibit 17: A true and correct excerpted copy of Chapter 1, Eyelid Anatomy, of a book by A. Biswas titled "Eyelid Tumors" (2014). Nov. 7, 2019.
Exhibit 18: A true and correct excerpted copy of Myco's Answer to Amended Counterclaims from *Myco Industries, Inc.* v. *BlephEx, LLC*, 2:19-cv-10645-GAD-EAS, Dkt. 41 (E.D. Mich.). Nov. 7, 2019.
Exhibit 19: A true and correct copy of a document titled Owner's Manual for the BlephEx product. Nov. 7, 2019.
Exhibit 20: A true and correct copy of a document titled Instructions for Use for the AB Max product. Nov. 7, 2019.
Exhibit 21: A true and correct copy of an FDA web page relating to the AB Max product. Nov. 7, 2019.
Exhibit 22: A true and correct copy of an FDA web page describing the Product Code PYU. Nov. 7, 2019.
Exhibit 23: A true and correct copy of Myco's web page www.ab-max.com/doctors/. Nov. 7, 2019.
Exhibit 24: A true and correct copy of Myco's web page at www.ab-max.com/doctors/how-it-works/. Nov. 7, 2019.
Exhibit 25: A true and correct copy of Myco's web page at www.ab-max.com/doctors/increase-profits/. Nov. 7, 2019.
Exhibit 26: A true and correct copy of BlephEx's web page at www.blephex.com/doctors/index.php. Nov. 7, 2019.
Exhibit 27: A true and correct copy of BlephEx's web page at www.blephex.com/doctors/index.php/how-does-blephex-work.html. Nov. 7, 2019.
Exhibit 28: A true and correct copy of a web page titled "BlephEx Treatment Offered in More Than 1,000 Ophthalmic Practices Worldwide" dated Apr. 28, 2015, at https://www.prnewswire.com/news-releases/blephex-treatment-offered-in-more-than-1000-ophthalmic-practices-worldwide-300073037.html. Nov. 7, 2019.
Exhibit 29: A true and correct copy of a web page titled "AOP Awards 2017 Product of the Year" at https://www.aop.org.uk/education-and-events/aop-awards/previous-years/2017/product-of-the-year;Scope. Nov. 7, 2019.
Exhibit 30: A true and correct copy of Myco's advertisement document named "Trade in Trade Up." Nov. 7, 2019.
Exhibit 32: A true and correct capture of Myco's Facebook page, captured on Oct. 27, 2019. Nov. 7, 2019.
Exhibit 33 is a true and correct copy of a document reflecting a web page post from Philip Wren. Nov. 7, 2019.
Exhibit 34 is a true and correct copy of a document reflecting a web page post from Steve Silberberg. Nov. 7, 2019.
Exhibit 35: Redacted. Nov. 7, 2019.
Exhibit 36: Redacted. Nov. 7, 2019.
Exhibit 37: Redacted. Nov. 7, 2019.
Exhibit 38: Redacted. Nov. 7, 2019.
Exhibit 39: Redacted. Nov. 7, 2019.
Exhibit 40: Redacted. Nov. 7, 2019.
Exhibit 41: Redacted. Nov. 7, 2019.
Exhibit 42: Redacted. Nov. 7, 2019.
Exhibit 43: Redacted. Nov. 7, 2019.
Exhibit 44: Redacted. Nov. 7, 2019.
Exhibit 45: Redacted. Nov. 7, 2019.
Exhibit 46: Redacted. Nov. 7, 2019.
Exhibit 47: A true and correct copy of Myco's web page at www.ab-max.com/doctors/. Nov. 7, 2019.
Exhibit 48: A true and correct copy the Court's Opinion and Order Denying Defendants' Motion to Dismiss from *Myco Industries, Inc.* v. *BlephEx, LLC*, 2:19-cv-10645-GAD-EAS, Dkt. 22 (E.D. Mich.). Nov. 7, 2019.
Exhibit 49: A true and correct copy of the opinion titled *Johns Hopkins Univ.* v. *Alcon Labs.*, No. 15-525, 2018 U.S. Dist. LEXIS 70403 (D. Del. Mar. 1, 2018). Nov. 7, 2019.
Exhibit 50: A true and correct copy of Mr. John E. Nemazi's Jun. 14, 2019 letter to me. Nov. 7, 2019.
Exhibit 51: A true and correct excerpted copy the Myco's Response Brief Opposing Defendants' Motion to Dismiss from *Myco Industries, Inc.* v. *BlephEx, LLC*, 2:19-cv-10645-GAD-EAS, Dkt. 20 (E.D. Mich.). Nov. 7, 2019.
Exhibit 52: A true and correct excerpted copy of the Myco's Amended Motion for Preliminary Injunction from *Myco Industries, Inc.* v. *BlephEx, LLC*, 2:19-cv-10645-GAD-EAS, Dkt. 11 (E.D. Mich.). Nov. 7, 2019.
Exhibit 53: A true and correct copy of Exhibit 1 (Declaration of John Choate) to the Myco's Amended Motion for Preliminary Injunction from *Myco Industries, Inc.* v.*BlephEx, LLC*, 2:19-cv- 10645-GAD-EAS, Dkt. 11-2 (E.D. Mich.). Nov. 7, 2019.
Exhibit 54: A true and correct copy of the opinion titled *Brocade Comm. Sys., Inc.* v. *A10 Networks, Inc.*, No. C 10-3428 PSG, 2013 WL 140039 (N.D. Cal. 2013). Nov. 7, 2019.
Exhibit 55: A true and correct copy of the opinion titled *Metso Minerals, Inc.* v. *Powerscreen Intern. Distribution Ltd.*, No. 06-cv-1446 (ADS)(ETB), 2011 WL 2149629 (E.D.N.Y. May 26, 2011). Nov. 7, 2019.
Exhibit 56: A true and correct copy of the opinion titled *Metalcraft of Mayville, Inc.* v. *Toro Co.*, No. 16-C-544, 2016 WL 4076894, (E.D. Wis. Aug. 1, 2016). Nov. 7, 2019.
Exhibit 57: A true and correct copy of the opinion titled *Cornucopia Prods., LLC* v. *Dyson, Inc.*, No. 12-234, 2012 WL 3094955 (D. Ariz. Jul. 27, 2012). Nov. 7, 2019.
Exhibit 58: A true and correct copy of a document titled Exhibit D—Individual Debtor's Statement of Compliance with Credit Counseling Requirement from in re John Raymond Choate, Jr. et al. (Bankr. E.D. Mich.). Nov. 7, 2019.
Exhibit 59: A true and correct excerpted copy of a transcript of the Feb. 1, 2017 deposition of *Mr. John Choate from Rysurg, LLC* v. *John R. Choate* , No. 2014-CA-000805XXXXMB(AG), Circuit Court of the 15th Judicial Circuit in and for Palm Beach County, Florida. Nov. 7, 2019.
Exhibit 60: A true and correct copy of U.S. Patent Publication No. 2013/0331768. Nov. 7, 2019.
Exhibit 61: A true and correct copy of Settlement Agreement and Release. Nov. 7, 2019.
Exhibit 62: A true and correct copy of Amendment to Settlement Agreement and Release. Nov. 7, 2019.
Canadian Intellectual Property Office, Office Action issued in corresponding Canadian Patent Application No. 2,873,219 dated Mar. 21, 2016 (3 pages).
Sue Stevens (NIH), How to Clean Eyelids, Community Eye Health Journal, 24(75):20, Sep. 2011 (15 pages) <http://www.cehjournal.

(56) References Cited

OTHER PUBLICATIONS org/article/how-to-clean-eyelids/> and <http://www.ncbi.nlm.nih.gov/pmc/articles/PMC3218399/>.

The Alger Company, Alger Brush Product Information (<http://www.algercompany.com/brush.product-info>), 2012 (2 pages).

*Blephex LLC* v. *Myco Industries, Inc.* and John R. Choate, Case No. 2:19-cv-13089-DML-APP, Exhibit 1, Invalidity Contentions for U.S. Pat. No. 10,449,087, filed Jun. 1, 2020, 21 pages.

*Blephex LLC* v. *Myco Industries, Inc.* and John R. Choate, Case No. 2:19-cv-13089-DML-APP, Exhibit 2, Invalidity Contentions for U.S. Pat. No. 10,449,087, filed Jun. 1, 2020, 30 pages.

*Blephex LLC* v. *Myco Industries, Inc.* and John R. Choate, Case No. 2:19-cv-13089-DML-APP, Exhibit 3, Invalidity Contentions for U.S. Pat. No. 10,449,087, filed Jun. 1, 2020, 20 pages.

*Blephex LLC* v. *Myco Industries, Inc.* and John R. Choate, Case No. 2:19-cv-13089-DML-APP, Exhibit 4, Invalidity Contentions for U.S. Pat. No. 10,449,087, filed Jun. 1, 2020, 21 pages.

*Blephex LLC* v. *Myco Industries, Inc.* and John R. Choate, Case No. 2:19-cv-13089-DML-APP, Exhibit 5, Invalidity Contentions for U.S. Pat. No. 10,449,087, filed Jun. 1, 2020, 25 pages.

*Blephex LLC* v. *Myco Industries, Inc.* and John R. Choate, Case No. 2:19-cv-13089-DML-APP, Exhibit 6, Invalidity Contentions for U.S. Pat. No. 10,449,087, filed Jun. 1, 2020, 21 pages.

*BlephEx LLC* v. *Myco Industries, Inc.* and John R. Choate, Case No. 2:19-cv-13089-GAD-EAS, USDC, Eastern District of Michigan, Defendant's Disclosure of Invalidity Contentions, filed Jun. 1, 2020, 15 pages.

Ocusoft [online retrieved on Jan. 8, 2015]. Retrieved from the internet at http://www.ocusoft.com/Foreign-Body-Removal-ALGERBRUSH-II-CHUCK-P4666.aspx Screen capture of page submitted herewith as "Algerbrush II Chuck with bilobal fitting".†

Rhein Medical, Inc. [online retrieved on Jan. 8, 2015]. Retrieved from the internet at http://www.rheinmedical.com/products-page/algerbrushes/08-13154-algerbrush-ii-chuck-2-5mm-roundfine-grit-diamond-ball/ Screen capture of page submitted herewith as "Algerbrush II chuck and round burr".†

The Alger Co., Inc. [online retrieved on Dec. 22, 2014]. Retrieved from the internet at http://www.algercompany.com/brush/2013/01/02/the-algerbrush-ii-2/ Screen capture of page submitted herewith as "Algerbrush II Product Page".†

The Alger Co., Inc. [online retrieved on Dec. 22, 2014]. Retrieved from the internet at http://www.algercompany.com/brush/pdf-file/ , click on "Operating/Sterilization Procedures" then click on "Algerbrush II Operating Instruction Rev 3 2012" to retrieve pdf submitted herewith as "Algerbrush-II-Operating-Instruct. 2012".†

\* cited by examiner
† cited by third party

INSTRUMENT FOR TREATING AN OCULAR DISORDER

CROSS-REFERENCE TO RELATED APPLICATION

This application is a continuation-in-part of U.S. application Ser. No. 13/556,729 filed Jul. 24, 2012, the disclosure of which is hereby incorporated by reference in its entirety.

TECHNICAL FIELD

The present invention relates generally to a method and apparatus for treating an ocular disorder, and more particularly, to treating eyelid margin disease.

BACKGROUND

Ocular disorders such as those relating to eyelid margin disease are particularly common pathological conditions of the ocular adenexa. By way of example, these disorders include blepharitis, meibomitis, and dry eye syndrome. Despite advances in ophthamology and medical treatments in general, the recommended treatments for these exemplary common ocular disorders has remained essentially unchanged for decades.

Historically, treatment of eyelid margin disease begins and ends with the patient. The patient first begins to notice symptoms including eyelid redness, flaking of skin on the eyelids, crusting and/or cysts at the eyelid margins, and a gritty sensation of the eye culminating in irritation, burning, and reduced vision. Should these symptoms remain unchanged or worsen, the patient routinely seeks the advice of an eye specialist, such as an ophthalmologist. After carefully considering the patients' medical history and investigating various possible causes, the specialist may prescribe a hygienic home treatment procedure for the patient to perform regularly in conjunction with antibiotics and/or topical steroids until the disease subsides.

The goal of the hygienic home treatment procedure is to remove debris, oil, and scurf that have collected along the eyelid margin during progression of the disorder. Removal of this debris is critical to both healing the eye and preventing a resurgence of the disorder. Without proper, regular removal of accumulated debris, such ocular disorders regularly worsen despite periodic treatments.

Hygienic home treatment of such ocular disorders is generally a two-step process. First, the patient softens the debris and scurf by applying a warm compress, diluted baby shampoo, or a specialized liquid solution to the eyelid margin. This first step is intended to prepare the debris for removal while preventing further irritation to the eye. Second, the patient attempts to remove the debris by physically scrubbing the eyelid margin, the base of the eyelashes, and the pores of the meibomian glands. This scrubbing is routinely attempted with either a generic cotton swab, a fingertip, or a scrub pad placed over the fingertip and applied against the eye. By cleaning debris and scurf free from the base of the eyelashes and unclogging the pores of the meibomian glands, the patient may improve the overall health of the eyelid margin; thereby reducing irritation, burning, and other symptoms related to the disorder.

Unfortunately for many patients, such hygienic home treatment is met with limited success due to the practical difficulties of cleaning one's own eye with an imprecise instrument such as a fingertip or cotton swab. For instance, many patients do not have the necessary dexterity to manipulate their fingertip or a cotton swab along the eyelid margin. Moreover, a shake, tremor, or poor near vision further complicate such self-treatment. Even for those capable of incorporating hygienic home treatment into their daily routine, many, if not most people, are wary of placing objects near their eyes to actively scrub along the eyelid margin. Given this anxiety, discomfort, and the inability to specifically target debris deposits, patients routinely fail to totally cleanse the margin of the eyelid, the base of the eyelashes, and the meibomian glands. While the attempted treatment may temporarily abate the patient's symptoms, subtle continuation of the disease often persists; thus permitting a low-grade inflammation to develop and, ultimately lead to chronic dry eye syndrome. Further, this treatment is typically required to be performed for the rest of the patient's life; thereby, creating a substantial hurdle to regular and effective compliance during hygienic home treatment.

Evidence suggests that medical costs associated with dry eye syndrome, often induced by ocular diseases such as blepharitis, are currently over 68 billion dollars each year. Many of these expenses are needlessly incurred due to the patients' failure to perform regular and effective treatments resulting in increased doctor visits, medications, and artificial tears. These expenses create a significant financial burden for insurance carriers, especially Medicare, which provides primary medical coverage for many individuals particularly prone to dry eye disease, such as the elderly.

There is a need for a method and apparatus for use in treating ocular disorders, such eyelid margin diseases, that addresses present challenges and characteristics such as those discussed above.

SUMMARY

One exemplary embodiment of an instrument for the removal of debris from an eye during the treatment of an ocular disorder has a swab and a rigid member. The swab includes a tip portion sized to provide access to the debris on an eyelid of the eye. The rigid member has a distal end portion and a proximal end portion. The distal end portion of the rigid member is affixed to the swab, and the proximal end portion has a cross-sectional member profile. The cross-sectional member profile of the proximal end portion is non-circular and has a first groove. The first groove extends longitudinally along the proximal end portion for cooperating with a chuck such that rotation of the proximal end portion within the chuck is inhibited.

One exemplary embodiment of a device for the removal of a debris from an eye during the treatment of an ocular disorder has a mechanical drive unit, a chuck, and an instrument. The chuck is connected to and is rotatably driven by the mechanical drive unit. The chuck also has an aperture extending at least partially therethrough with a cross-sectional aperture profile. The instrument is removably secured within the aperture and has a swab and a rigid member. The swab includes a tip portion sized to provide access to the debris on an eyelid of the eye. The rigid member has a distal end portion and a proximal end portion. The distal end portion of the rigid member is affixed to the swab, and the proximal end portion has a cross-sectional member profile configured to cooperate with the cross-sectional aperture profile of the aperture such that rotation of the proximal end portion within the aperture is inhibited. Accordingly, the mechanical drive unit rotatably drives the instrument via the chuck for removing debris.

Various additional objectives, advantages, and features of the invention will be appreciated from a review of the following detailed description of the illustrative embodiments taken in conjunction with the accompanying drawings.

BRIEF DESCRIPTION OF THE DRAWINGS

The accompanying drawings, which are incorporated in and constitute a part of this specification, illustrate embodiments of the invention and, together with a general description of the invention given above, and the detailed description given below serve to explain the invention.

DETAILED DESCRIPTION

Figure 1:
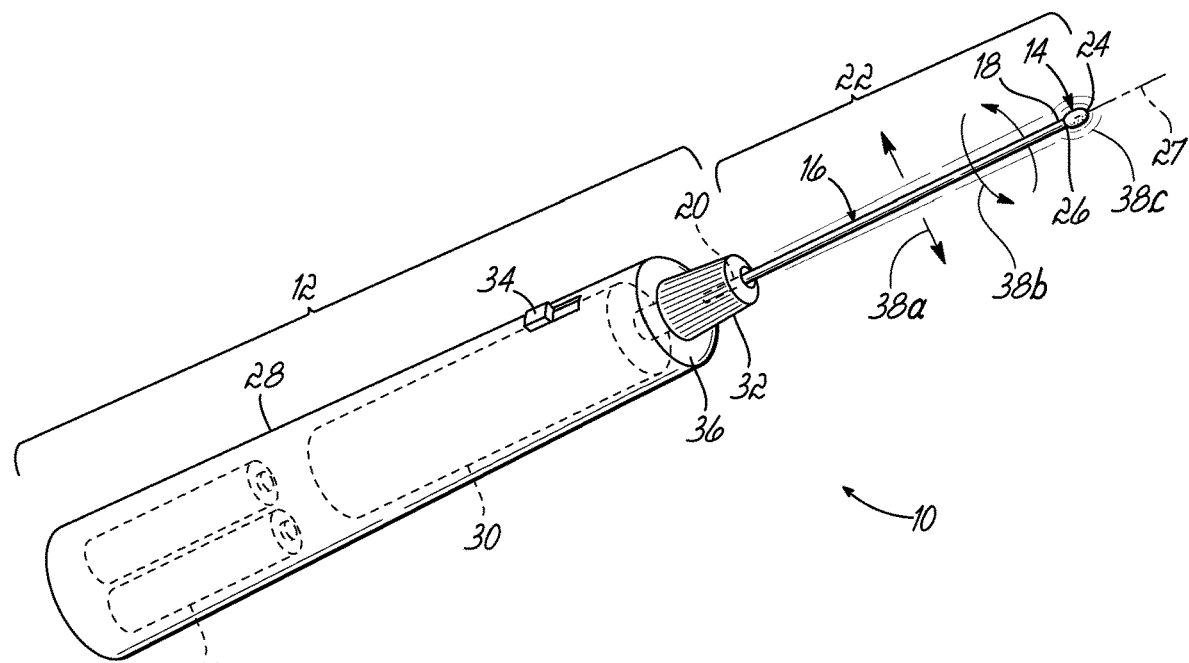
FIG. 1 is a perspective drawing of one embodiment of the device.
Figure 5A:
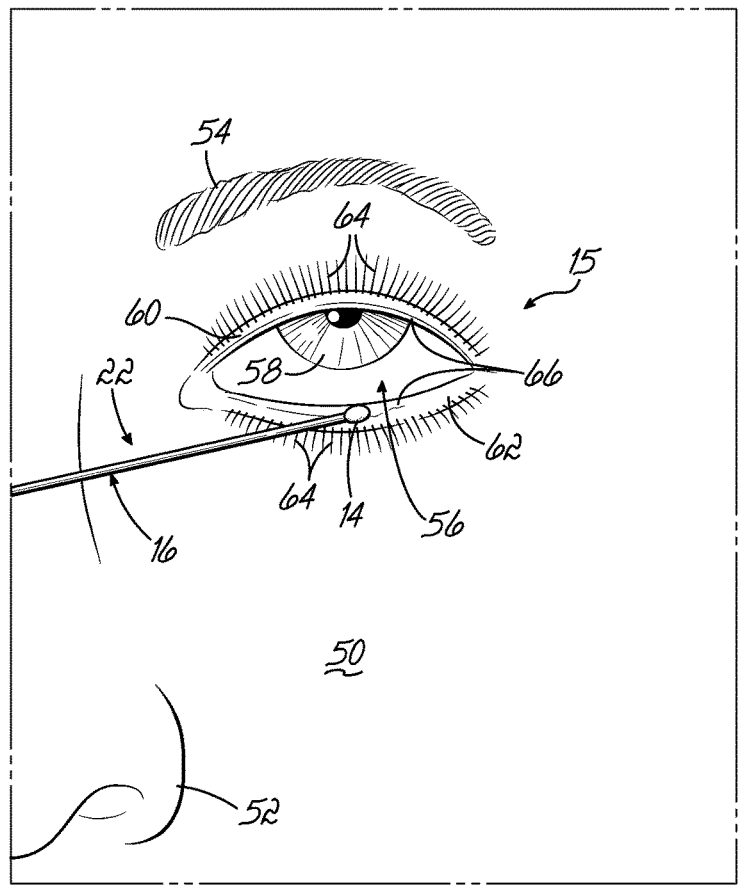
FIG. 5A is a drawing of the device of FIG. 1 treating a lower eyelid margin of an eye.
Figure 5B:
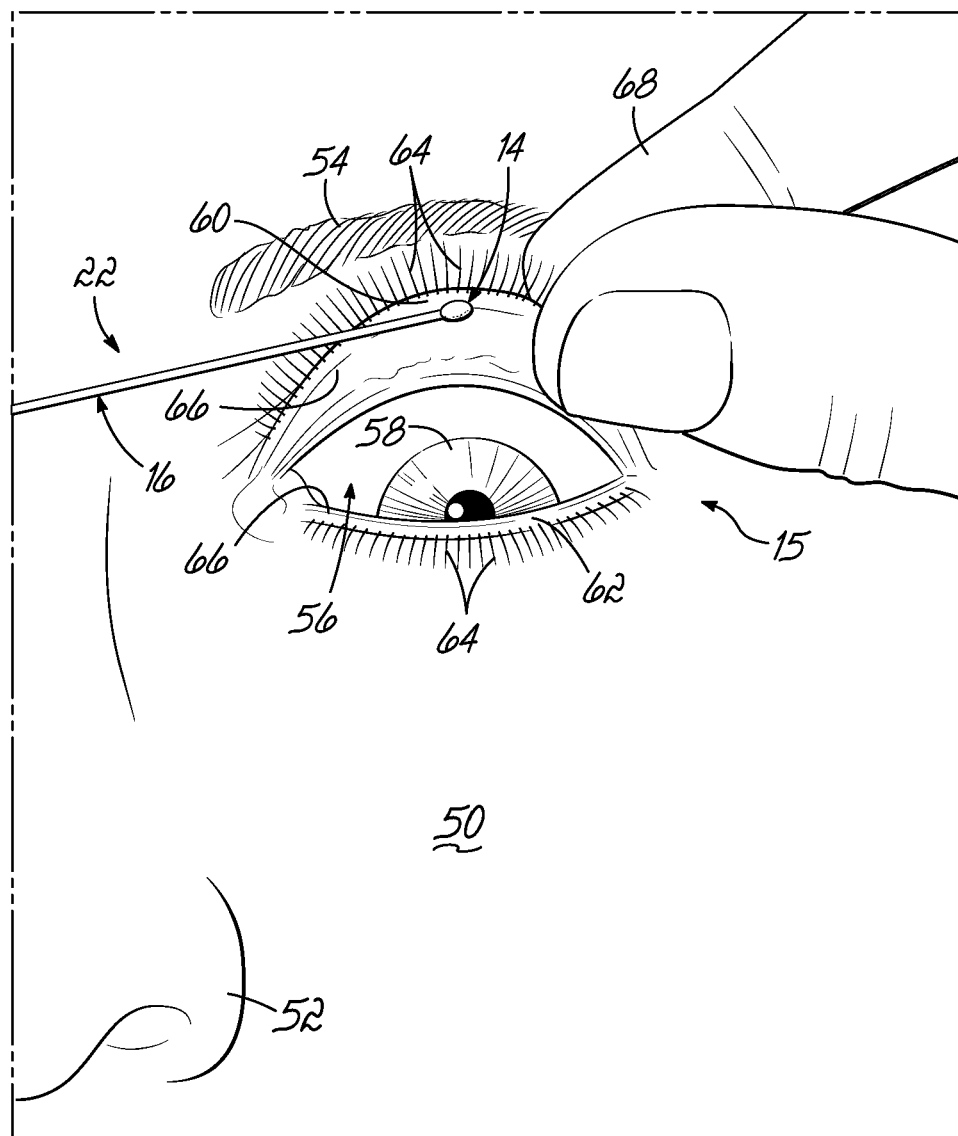
FIG. 5B is a drawing of the device of FIG. 1 treating a upper eyelid margin of an eye.

With reference to FIG. 1, an embodiment of the device 10 for treating an ocular disorder, particularly with respect to eyelid margin diseases, includes a mechanical drive unit 12 which operably moves a swab 14 to facilitate removal of debris from an eye 15 (see FIGS. 5A-5B). The swab 14 is connected to a rigid member 16 having both a distal end portion 18 and a proximal end portion 20. The swab 14 is affixed to the distal end portion 18 of the rigid member 16 to create an instrument 22, which may be secured to the mechanical drive unit 12. As shown in FIG. 1, the proximal end portion 20 is removably secured to the mechanical drive unit 12 in order to transmit motion from the mechanical drive unit 12, through the rigid member 16, and to the swab 14. It will be appreciated that any known method may be used to removably secure the instrument 22 to the mechanical drive unit 12. Moreover, it will also be appreciated that device 10 is not intended to be limited to the instrument 22 being removably secured to the mechanical drive unit 12. For instance, in another embodiment, the rigid member 16 may be either permanently secured or removably secured to either one of the swab 14 and/or the mechanical drive unit 12.

In one aspect of the instrument 22, the swab 14 includes a tip portion 24 and a base portion 26. While the swab 14 may be of a size sufficient to access debris on the eye 15 as shown in FIGS. 1, 5A, and 5B, at least the tip portion 24 is of a size sufficient to access debris on the eye 15. For instance, the swab 14 has an approximate length between 1.0-3.0 millimeters and an approximate width of between 0.5-1.5 millimeters. More particularly, the swab 14 has an approximate length of 2 millimeters and an approximate width of 1 millimeter. It will be appreciated that the swab 14 may be manufactured of any material suitable for contacting the eye 15 without harming the eye 15. However, as shown in the embodiment of FIG. 1, the swab 14 is a sponge. As described herein, "sponge" broadly refers to any material that is soft, porous, and resilient. Particularly, the swab 14 is a medical grade sponge or a surgical grade sponge capable of removing debris from on the eye 15 without harming the eye 15. As shown in the exemplary embodiment of FIG. 1, the swab 14 is a methyl cellulose sponge. It will be appreciated; however, that similar materials capable of removing debris from on the eye 15 without harming the eye 15 are readily apparent and may also be used.

In another aspect of the instrument 22, the rigid member 16 is a plastic, cylindrical shaft including a central axis 27. The shaft extends along the central axis 27 between the mechanical drive unit 12 and the swab 14. The rigid member 16 is sufficiently rigid to effectively transmit motion from the mechanical drive unit 12 to the swab 14. As shown in FIG. 1, the swab 14 is permanently affixed to the distal end portion 18 by forming the base portion 26 to the rigid member 16 during manufacturing. However, it will be appreciated that any known method of affixing the swab 14 to the rigid member 16 may be used. In an exemplary embodiment, any material or shaft shape may be used so long as the rigid member 16 is rigid enough to transmit sufficient motion from the mechanical drive unit 12 to the swab 14 in order to remove debris from on the eye 15.

Furthermore, the mechanical drive unit 12 includes a body 28, an electric motor 30, a chuck 32, and a control switch 34. As such, the device 10 is electromechanical in nature. In an exemplary embodiment, the electric motor 30, the chuck 32, and the control switch 34 are integrated into the body 28 so that the electromechanical device 10 is configured to be handheld as shown in FIG. 1. However, the electromechanical device 10 is not intended to be limited to a handheld configuration, and it will be appreciated that other configurations of the device 10 are readily apparent.

According to the present embodiment, the electric motor 30 is positioned within the body 28. The chuck 32 is operably connected to the electric motor 30 at a forward end portion 36 of the body 28. The proximal end portion 20 of the rigid member 16 is removably secured to the chuck 32. As described herein, the chuck 32 is generally any element capable of removably securing the rigid member 16 to the mechanical drive unit 12. As such, the chuck 32 may be tightened or loosened to respectively secure or remove the instrument 22 to the chuck 32. Thereby, the operable connection of the electric motor 30 transmits a movement 38 through the chuck 32 to the instrument 22. The movement 38 is any motion relative to the mechanical drive unit 12 or, more particularly, to the body 28, that creates relative motion to the debris on the eye 15 such that upon contacting the debris with the swab 14, the debris is removed. As shown, the movement 38 may include, but is not limited to, a reciprocating movement 38a, a rotating movement 38b, or a vibrating movement 38c. The reciprocating movement 38a may be either along the central axis 27 of the rigid member 16 or orthogonal to the central axis 27 of the rigid member 16. In addition, the speed of the movement 38 of the swab 14 is any speed sufficient to remove debris from on the eye 15. It will be appreciated that the speed discussed herein collectively refers to both relative speed of the swab 14 and the frequency of the movement 38 of the swab 14. For instance, the frequency may range from sonic frequencies to ultrasonic frequencies. Furthermore, the speed of the swab 14 may be variable or otherwise selectable such that an operator of the device 10 may select a desirable speed or a forward or reverse direction via the control switch 34.

Moreover, the control switch 34 is operably connected to the electric motor 30 and an electric power source 42 to power the device 10 on and off. In an exemplary embodiment, the electric power source 42 is a battery power source 42 contained within the body 28. The battery power source 42 may be either disposable or rechargeable. The electric power source 42 operably provides electrical power to the electric motor 30, which the operator controls via the control switch 34. It will be appreciated that any known control switch 34 or plurality of control switches 34 may be configured to power the device 10 on and off.

Furthermore, it will be appreciated that the device 10 may be manufactured from various materials suited to specific environments of use. For instance, operators within the professional clinic setting may desire a durable, reusable mechanical drive unit 12 and single-use instruments 22. Some examples of such a professional mechanical drive unit 12 is an Algerbrush I, an Algerbrush II, or similar medical device. However, operators within the home treatment setting may desire the device 10 to be generally disposable and single-use.

Figure 2:
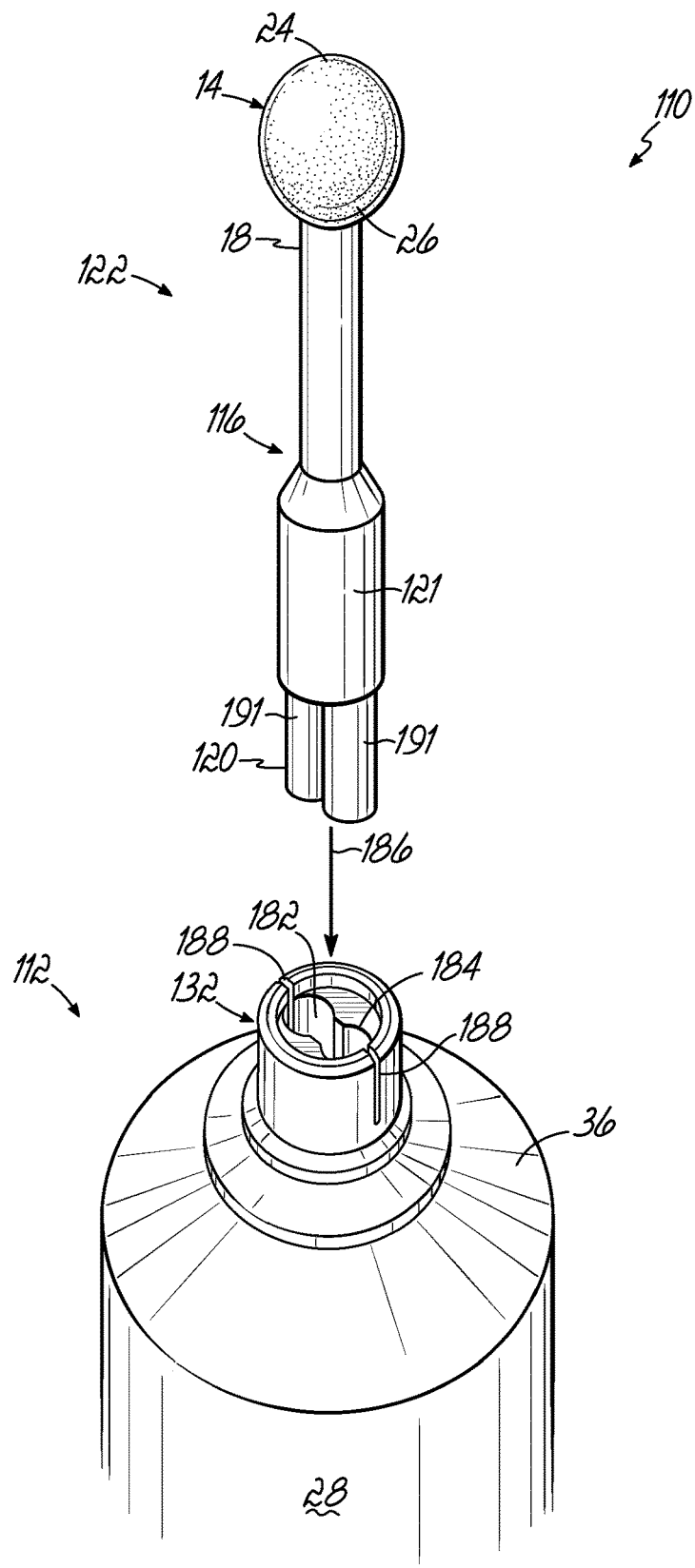
FIG. 2 is a partially exploded perspective view of another embodiment of the device.
Figure 2B:
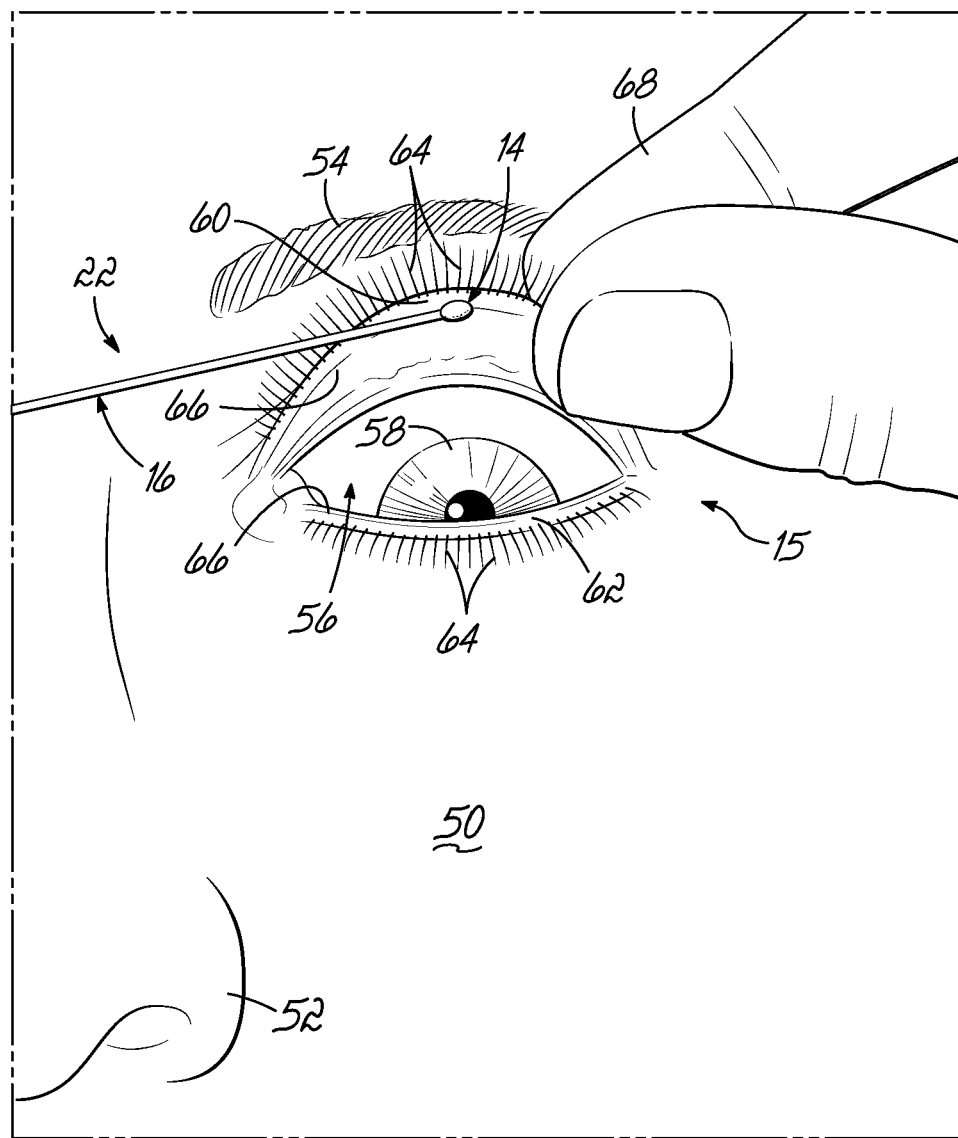
Figure 4:
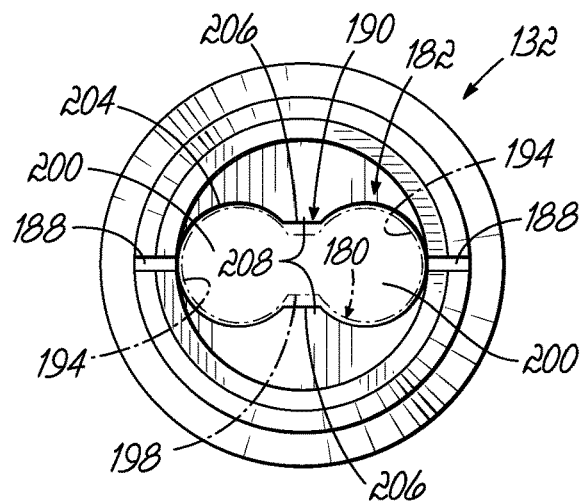
FIG. 4 is a top view of the chuck having a cross-sectional profile of the instrument in phantom lines.
Figure 3A:
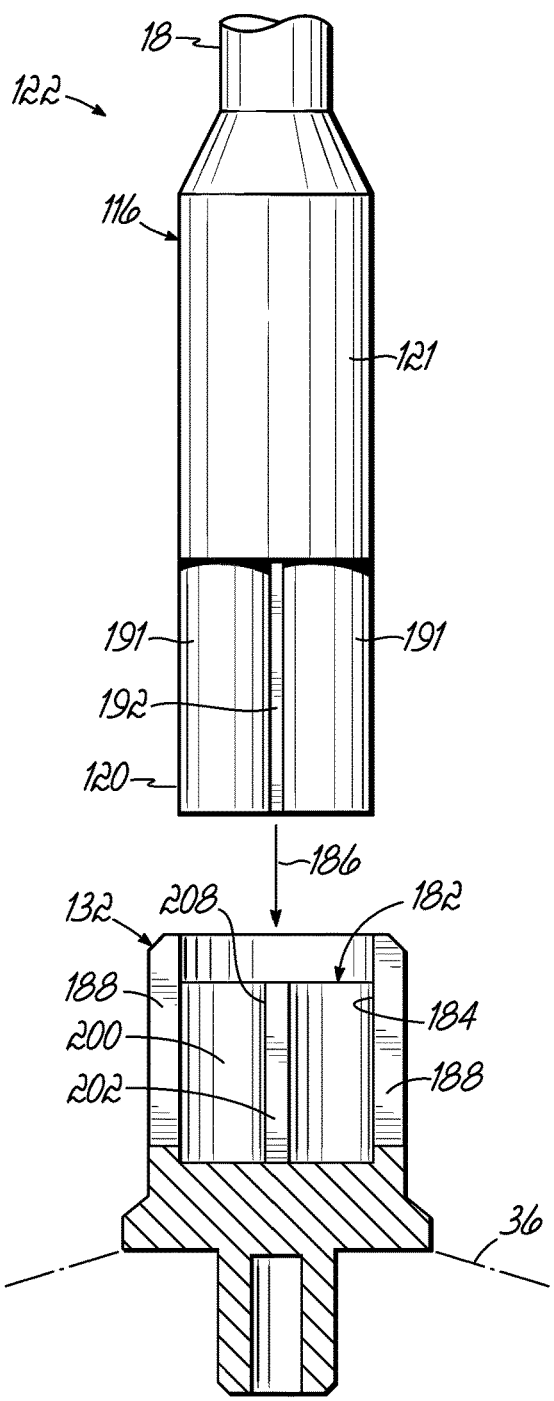
FIG. 3A is an enlarged front view of the device of FIG. 3.
Figure 3B:
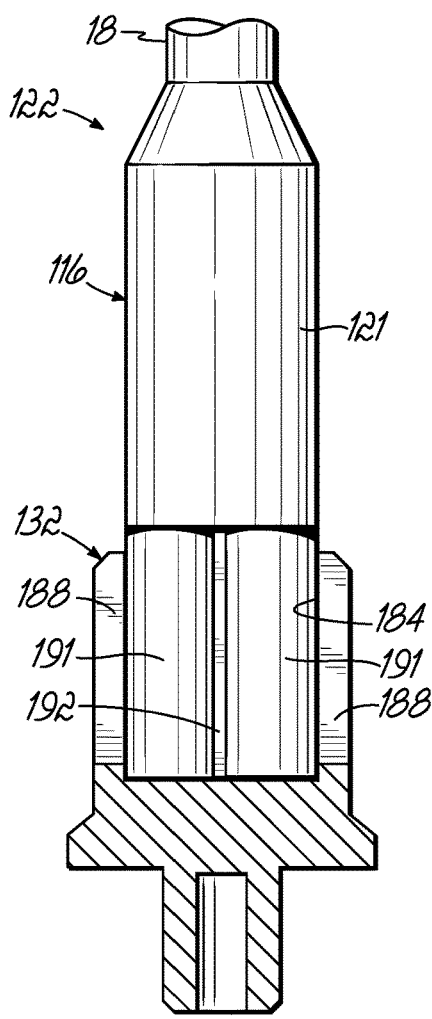
FIG. 3B is an enlarged front view of the device similar to FIG. 4A, but showing an instrument removably secured to a chuck.

FIGS. 2-4 show another embodiment of a device 110 for treating an ocular disorder. The device 110 includes an instrument 122 removably secured to a mechanical drive unit 112. The device 110 provides for safe, simple, and reliable removal and replacement of disposable, single-use instruments 122 between treatments. Specifically, the mechanical drive unit 112 has a chuck 132 projecting from the forward end portion 36 of the body 28 and configured for unique frictional engagement with the instrument 122. In this respect, the attachment between the chuck 132 and the instrument 122 discourages improper installation and inhibits the use of other, unsuitable instruments that may create unnecessary risk of damaging the eye 15 (see FIG. 5A) during use. Moreover, the instrument 122 and chuck 132 provide for simple frictional attachment via insertion and withdrawal (i.e., push-in and pull-out) of the instrument 122 without collars, clasps, or other mechanisms. The chuck 132 also effectively transmits torque to the instrument 122 without generating damaging stress concentrations in either the instrument 122 or the chuck 132. The instrument 122 includes a rigid member 116 having the swab 14 projecting from the distal end portion 18 and, as such, like numbers for the device 110 refer to like features previously described above.

With respect to FIG. 2, the rigid member 116 further includes a proximal end portion 120 sized for insertion into the chuck 132 and an intermediate portion 121 extending between the distal end portion 18 and the proximal end portion 120. The intermediate portion 121 and the distal end portion 18 are both generally cylindrical; however, the intermediate portion 121 has a larger diameter than the distal end portion 18 and tapers toward the distal end portion 18. Also, the proximal end portion 120 has a width that is generally as wide as the diameter of the intermediate portion 121, but a depth generally less than the diameter of the intermediate portion 121 as shown in FIG. 4. However, it will be appreciated that the relative sizes of the portions of the instrument 122, such as diameters, widths, and depths, may vary in accordance with the invention described herein.

With respect to FIGS. 2-4, the proximal end portion 120 has a cross-sectional member profile 180 that inserts into an aperture 182 and frictionally engages a sidewall 184 of the chuck 132 for removably attaching the instrument 122 to the mechanical drive unit 112. Thus, the proximal end portion 120 may be inserted into the aperture 182 as indicated by arrow 186 and withdrawn in the opposite direction to remove the instrument 122 from the chuck 132. The frictional engagement is generally created by the proximal end portion 120 being sized with an interference fit within the aperture 182 against the sidewall 184. However, the engagement is enhanced by a pair of opposing slots 188 extending longitudinally through the sidewall 184. The slots 188 create resiliency within with sidewall 184 that further aid in frictionally engaging the proximal end portion 120 of the instrument 122. In addition, as the aperture 182 receives the proximal end portion 120, the slots 188 vent ambient air from within the aperture 182 to inhibit air pressure buildup that may force the instrument 122 from the chuck 132 after insertion. However, it will be appreciated that other structures may be used to create resiliency and vents. For example, the chuck 132 may be manufactured from a relatively resilient material, and the aperture 182 may include a vent of any shape through another portion of the chuck 132 for releasing air pressure. In an alternative embodiment, the proximal end portion 120 may be removably attached to the chuck 132 via other structures or connectors, such as a collar or clasp. In any case, the invention is not intended to be limited to the exemplary embodiments described herein.

FIGS. 3A-4 show an exemplary embodiment of the cross-sectional member profile 180 defined by the proximal end portion 120 that inserts into the aperture 182, at least a portion of which has a cross-sectional aperture profile 190 for frictionally mating with the cross-sectional member profile 180. The cross-sectional member profile 180 is generally longitudinally uniform along the proximal end portion 120 with a constant cross-section. However, it will be appreciated that the proximal end portion 120 may taper toward the chuck 132 or have another suitable shape for insertion into the aperture 182 in an alternative embodiment.

More particularly, the proximal end portion 120 has a pair of generally parallel cylindrical portions 191 connected by a generally linear tab portion 192 therebetween. As such, the proximal end portion 120 defines the cross-sectional member profile 180 as a pair of curved, opposing major arc surfaces 194 connected by a pair of opposing linear surfaces 196. Accordingly, the generally cylindrical portions 191 at least partially define a groove 198 extending longitudinally along the proximal end portion 120. According to an exemplary embodiment, the linear tab portion 192 and generally cylindrical portions 120 define a pair of opposing grooves 198 extending longitudinally along the proximal end portion 120.

In order to receive the proximal end portion 120 of the instrument 122, the sidewall 184 defines at least a portion of the aperture 182 with the cross-sectional aperture profile 190. As such, the cross-sectional aperture profile 190 has similar, mating surfaces to the cross-sectional member profile 180. The aperture 182 has a pair of generally parallel cylindrical hole portions 200 connected by a generally linear slot portion 202 therebetween. The proximal end portion 120 thus defines the cross-sectional aperture profile 190 as a pair of curved, opposing major arc surfaces 204 connected by a pair of opposing linear surfaces 206. Accordingly, the generally cylindrical hole portions 200 and linear slot portion 202 define a pair of opposing projections 208 extending longitudinally along the sidewalls 184 within the aperture 182.

As the chuck 132 is operatively rotated, the sidewall 184 transmits torque to the proximal end portion 120 and, in turn, rotates the instrument 122. Effectively, each projection 208 is keyed to the respective groove 198 for transmitting the torque. Furthermore, the exemplary embodiment of the cross-sectional aperture profile 190 inhibits insertion of unsuitable instruments while continuing to effectively engage the proximal end portion 120 with many stress-reducing curved surfaces. However, it will be appreciated that the exemplary embodiment of the aperture 182 and the proximal end portion 120 may be other cooperating shapes providing for removable attachment. To the extent other profiles may function similarly to the embodiment described above, it will be appreciated that the exemplary embodiment of the instrument 122 shown in FIGS. 2-4 may have ornamental characteristics, as well.

With respect to FIGS. 5A and 5B, the device 10 is used in a method for treating ocular disorders of the eye 15. While the method for treating ocular disorder will be described with respect to device 10, it will be appreciated that the device 110 (see FIG. 2) may be similarly used. For purposes of describing the environment in which this method occurs, FIGS. 5A and 5B generally show a portion of a face 50 having a nose 52, an eyebrow 54, and the eye 15. The eye 15 described herein generally includes, but is not limited to, an eyeball 56 including a cornea 58, an upper eyelid margin 60, a lower eyelid margin 62, and a plurality of eyelashes 64. In the exemplary embodiment, the device 10 is the swab 14 operably connected to the mechanical drive unit 12 thereby creating the electromechanical device 10 for use in removing debris deposited on at least one of either the upper eyelid margin 60 or the lower eyelid margin 62.

As shown in FIG. 1, an instrument 22 is removably secured to the chuck 132, after which time, the electromechanical device 10 may be powered on and set to a desirable speed by the operator; thereby, the operator effects movement of the swab 14 relative to the electromechanical device 10. Such movement may include, but is not limited to, reciprocating the swab 14 as shown by arrows 38a, rotating the swab 14 as shown by arrow 38b, and/or vibrating the swab 14 as shown by lines 38c. The swab 14 is positioned near the eyeball 56 and along either one of the upper or lower eyelid margins 60, 62 for treatment. In the exemplary embodiment as shown in FIGS. 5A and 5B, the swab 14 moves with constant movement relative to the electromechanical device 10 while near the eyeball 56. Alternatively, it may be desirable to vary the movement of the swab 14 relative to the electromechanical device 10 such that the operator has greater control of treating the ocular disorder.

In an exemplary embodiment, the operator preferably targets the debris present on the eye 15 with the swab 14 of the electromechanical device 10. The debris may be targeted by visually inspecting the eye 15 with or without the aid of a magnification device. Once the debris is targeted, the swab 14 contacts the portion of the eye 15 that includes the debris. For purposes of treating the ocular disorder, the debris may be removably attached on either the upper and lower eyelid margins 60, 62 or the plurality of eyelashes 64. Thereby, upon contacting the portion of the eye 15 with the debris, the swab 14 impacts the debris to remove the debris from the eye 15. Furthermore, a liquid solution configured to loosen the debris may be absorbed within the swab 14 to further aid in removing the debris from the eye 15 and/or minimizing irritation to the eye 15. It will be appreciated that any liquid solution sufficiently capable of loosening the debris to further aid in removing the debris may be so used.

The electromechanical device 10 operably drives the swab 14 to break the debris free from either of the upper or lower eyelid margins 60, 62. Further treatment may be performed to enhance the effects of the debris removal by helping to improve healing and reducing further infection of the eye 15. Such treatment may include scrubbing, exfoliating, or buffing the eyelid margin or un-roofing a meibomian gland 66 with the swab 14.

In another aspect, the cornea 58 of the eye 15 is directed away from the position of the swab 14 to minimize contacting the swab 14 to the cornea 58 during treatment. As shown in FIG. 5A, while treating the lower eyelid margin 62, the eyeball 56 directs the cornea 58 upward, thereby bringing the cornea 58 closer to the upper eyelid margin 60 than the lower eyelid margin 62. However, as shown in FIG. 5B, while treating the upper eyelid margin 60, the eyeball 56 directs the cornea 58 downward, thereby being closer to the lower eyelid margin 62 than the upper eyelid margin 60.

As shown in FIG. 5A, accessing the portion of the eye 15 with the debris, such as the upper or lower eyelid margins 60, 62, may be accomplished without further moving or lifting other portions of the eye 15. However, as shown in FIG. 5B, if accessing the portion of the eye 15 with the debris is difficult, the operator may use a hand 68, or similar gripping device, to move or lift a portion of the eye 15, such as lifting the upper or lower eyelid margin 60, 62 from against the eyeball 56, to improve access to the debris. Such lifting may be particularly beneficial for improving access to the meibomian gland 66. It will be appreciated that, in order to improve access to the debris, any portion of the eye 15 may be moved or lifted regardless of which eyelid margins 60, 62 are being treated. FIGS. 5A and 5B are merely exemplary embodiments showing both non-assisted access and assisted access of the swab 14 to the eye 15 respectively.

Furthermore, the method of treating the ocular disorder may be repeated as directed by a physician or patient in order to sufficiently remedy the disorder. For instance, in the case of physician directed treatment, the physician may direct the patient to visit the physician in periodic intervals for treating the ocular disorder with the electromechanical device 10. More specifically, the physician directs the patient to visit the physician in periodic monthly or weekly intervals so that the physician may treat the patient. In the exemplary embodiment, periodic intervals are treatments with the electromechanical device 10 once every month. It will be appreciated that any periodic interval of repeating the method of treating the ocular disorder with the electromechanical device 10 may be so used.

Alternatively, in the case of home treatment by the patient, the patient may treat his or her own ocular disorder with the electromechanical device 10 in periodic intervals. However, according to the exemplary embodiment, the physician repeats the method of treating the ocular disorder in periodic intervals with the electromechanical device 10 and the patient also treats the ocular disorder in between physician treatments using traditional treatments. This method of treating the ocular disorder with the electromechanical device 10 in treatments occurring in periodic intervals achieves superior removal of the debris compared to traditional treatments, because the periodic intervals act as reminders to the patient. Thus, the patient is less likely to forget to treat the ocular disorders once symptoms begin to subside, which may result in a resurgence of the disorder. However, the traditional treatments, despite being less effective, may be performed regularly by the patient to further treat the ocular disorder in conjunction with physician treatments with the electromechanical device 10.

In any case, the physician or patient treats the ocular disorder until the ocular disorder is sufficiently healed and thereafter to prevent a recurrence of the disorder. It will be appreciated that sufficiently healed refers to the dissipation of inflammation and/or discomfort related to the debris within the eye 15 at which time the treatments by the physician may decrease in frequency, but may continue in periodic intervals during home treatment by the patient. After each treatment, the physician or patient may remove the used instrument 22 from the chuck 32 and dispose of the used instrument 22. The used instrument 22 may then be replaced with a new instrument 22 for future treatments. In the event that the inflammation, discomfort, or debris worsens, the method of treating the ocular disorder may resume as the physician or patient desires. However, the treatment may be required in periodic intervals throughout the remainder of the patient's life.

While the present invention has been illustrated by the description of one or more embodiments thereof, and while the embodiments have been described in considerable detail, they are not intended to restrict or in any way limit the scope of the appended claims to such detail. Additional advantages and modifications will readily appear to those skilled in the art. The invention in its broader aspects is therefore not limited to the specific details, representative apparatus and method and illustrative examples shown and described. Accordingly, departures may be from such details without departing from the scope or spirit of the general inventive concept.

What is claimed is:

1. A device for the removal of a debris from an eye during the treatment of an ocular disorder, comprising;
   a mechanical drive unit;
   a chuck connected to and rotatably driven by said mechanical drive unit, said chuck having an aperture extending at least partially therethrough, said aperture being formed by sidewalls separated by a slot and having a cross-sectional aperture profile defined by a pair of curved surfaces and a pair of linear surfaces connected to each of said pair of curved surfaces;
   an instrument removably secured within said aperture, said instrument comprising:
      a swab having a tip portion, said tip portion being sized to provide access to the debris on an eyelid margin of the eye; and
      a rigid member having a distal end portion and a proximal end portion, said distal end portion affixed to said swab, said proximal end portion having a cross-sectional member profile configured to cooperate with said cross-sectional aperture profile of said aperture such that rotation of said proximal end portion within said aperture is inhibited, wherein said cross-sectional member profile of said proximal end portion is non-circular and is defined by first and second curved portions, the first curved portion including a first curved major convex arc surface about a first center, the second curved portion including a second curved major convex arc surface about a second center, the first center and the second centers being offset from each other, and a linear tab portion extending between and connecting the pair of curved portions, said linear tab portion including opposing linear surfaces, each of which is directly connected to both of said curved major arc surfaces of said pair of curved portions, such that the cross-sectional member profile has a first groove located at a gap between said pair of curved portions and along one of said opposing linear surfaces, and wherein said proximal end portion is sized to form an interference fit with the sidewalls when inserted into said aperture of said chuck,
   wherein said mechanical drive unit rotatably drives said instrument via said chuck for removing the debris, and wherein the securing of said instrument to said chuck transmits the movement of said mechanical drive unit to said instrument, including at least one of reciprocating movement, vibrating movement, and rotary movement.

2. The device of claim 1 wherein said cross-sectional aperture profile and said cross-sectional member profile have generally the same shape for removable insertion of the proximal end portion within the mounting aperture.

3. The device of claim 2 wherein said cross-sectional aperture profile has a first projection extending longitudinally along said aperture and said first projection and said first groove being keyed together for further securing said instrument within said aperture.

4. The device of claim 3 wherein said cross-sectional aperture profile has a second projection opposed from said first projection and said cross-sectional member profile has a second groove opposed from said first groove, said second groove positioned at another gap between said pair of curved portions and along another of said opposing linear surfaces, said second projection extending longitudinally along said aperture and said second groove extending longitudinally along said proximal end portion, and said second projection and said second groove being keyed together for further securing said instrument within said aperture.

5. The device of claim 1 wherein said cross-sectional aperture profile is non-circular.

6. The device of claim 1 wherein the slot extends through the sidewalls enabling venting during insertion of the instrument into the aperture.

* * * * *